United States Patent [19]

Zahir

[11] Patent Number: 4,560,739
[45] Date of Patent: Dec. 24, 1985

[54] TRIGLYCIDYL COMPOUNDS OF AMINOPHENOLS

[75] Inventor: Abdul-Cader Zahir, Oberwil, Switzerland

[73] Assignee: Ciba-Geigy Corporation, Ardsley, N.Y.

[21] Appl. No.: 673,074

[22] Filed: Nov. 19, 1984

[30] Foreign Application Priority Data

Dec. 2, 1983 [CH] Switzerland .................... 6467/83

[51] Int. Cl.$^4$ .................... C08G 59/28; C08G 59/02
[52] U.S. Cl. .................... 528/99; 528/103; 252/182; 549/552
[58] Field of Search .................... 528/99, 103; 549/552; 252/182

[56] References Cited

U.S. PATENT DOCUMENTS

| | | | |
|---|---|---|---|
| 2,951,822 | 9/1960 | Reinking | 528/103 |
| 2,951,825 | 9/1960 | Reinking et al. | 528/99 |
| 3,418,371 | 12/1968 | Krimm et al. | 564/315 |

FOREIGN PATENT DOCUMENTS 1176666  8/1964  Fed. Rep. of Germany .

OTHER PUBLICATIONS

Chem. Abstr. 101, 131818z, (1984).
Lee et al., Handbook of Epoxy Resins, 2-21 (1967).
Journal of Applied Polymers Science, 26, 2363-2372, (1981).

Primary Examiner—Earl Nielsen
Attorney, Agent, or Firm—Harry Falber

[57] ABSTRACT

Triglycidyl compounds of the formula I

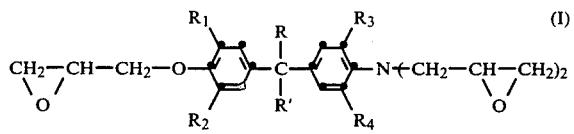

and epoxy resin mixtures containing a triglycidyl compound of the formula I and a tetraglycidyl compound of the formula II

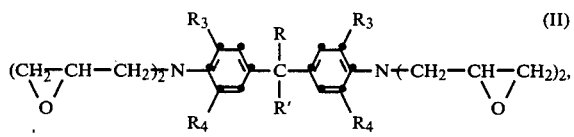

in which formulae each of R and R' independently is a hydrogen atom, $C_1$-$C_6$ alkyl, phenyl, cyclohexyl or cyclopentyl, and each of $R_1$, $R_2$, $R_3$ and $R_4$ independently is a hydrogen atom, a halogen atom, or $C_1$-$C_6$ alkyl.

Thses compounds are valuable epoxy resins which are also suitable for the preparation of B-stage resins.

10 Claims, No Drawings

TRIGLYCIDYL COMPOUNDS OF AMINOPHENOLS

The present invention relates to novel triglycidyl compounds based on unsubstituted or ring-substituted 4-hydroxyphenyl-4-aminophenylalkanes, to mixtures of epoxy resins containing said novel triglycidyl compounds and tetraglycidyl compounds of specific aromatic diamines, as well as to the use of the novel triglycidyl compounds, and of the epoxy resin mixtures containing them, in curable mixtures.

Trifunctional and tetrafunctional glycidyl compounds are of interest for many technical applications on account of the properties which they confer on the moulding compositions prepared from these epoxy resins by curing or crosslinking and shaping. Thus, for example, N,N-diglycidyl-4-aminophenolglycidyl ethers and N,N,N',N'-tetraglycidyl bis(4-aminophenyl)methane are known compounds which are available commercially. As is apparent from the investigations described in the Journal of Applied Polymer Science, Vol. 26, 2363–2372 (1981), these glycidyl compounds have the drawback that they are sensitive to moisture, so that appropriate measures have to be taken when storing and handling these epoxy resins. Furthermore, both glycidyl compounds react very readily with curing agents for epoxy resins (q.v H. Lee and K. Neville, Handbook of Epoxy Resins (1967), 2–21), so that B-stage resins cannot be obtained, or can only be obtained with difficulty, from them.

It has now been found that triglycidyl compounds based on unsubstituted or ring-substituted 4-hydroxyphenyl-4-aminophenylalkanes, both by themselves and in admixture with tetraglycidyl compounds of specific aromatic diamines, are less sensitive to moisture and, in particular, are suitable or more suitable for the preparation of B-stage resins.

Accordingly, the present invention relates to triglycidyl compounds of the formula I

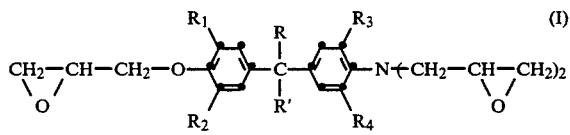

wherein each of R and R' independently is a hydrogen atom, $C_1$–$C_6$-alkyl, phenyl, cyclohexyl or cyclopentyl, and each of $R_1$, $R_2$, $R_3$ and $R_4$ independently is a hydrogen atom, a halogen atom or $C_1$–$C_6$alkyl, and to epoxy resin mixtures containing (a) a triglycidyl compound of the formula I and (b) a tetraglycidyl compound of the formula II

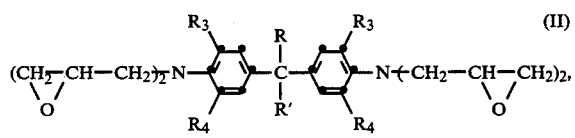

wherein R, R', $R_3$ and $R_4$ are as defined for formula I, the ratio of the epoxide equivalents of (a) to (b) in said epoxy resin mixtures being 10:1 to 1:10.

Preferably, the invention relates to triglycidyl compounds of the formula I, wherein each of R and R' is a hydrogen atom or methyl, preferably methyl, and each of $R_1$, $R_2$, $R_3$ and $R_4$ independently is a hydrogen, chlorine or bromine atom or alkyl of up to 4 carbon atoms. A particularly interesting triglycidyl compound of the formula I is 2,2-(N,N-diglycidyl-4-aminophenyl-4'-glycidyloxyphenyl)propane.

The epoxy resin mixtures of this invention preferably contain a triglycidyl compound of the formula I and a tetraglycidyl compound of the formula II, wherein each of R and R' is a hydrogen atom or methyl, and each of $R_1$, $R_2$, $R_3$ and $R_4$ independently is a hydrogen, chlorine or bromine atom or $C_1$–$C_4$alkyl.

A particularly preferred epoxy resin mixture contains 2,2-(N,N-diglycidyl-4-aminophenyl-4'-glycidyloxyphenyl)propane as compound of formula I and N,N,N',N'-tetraglycidyl-4,4'-diaminodiphenylmethane as compound of formula II.

Further, the ratio of the epoxide equivalents of (a) to (b) in the epoxy resin mixture of this invention is preferably 5:1 to 1:5, most preferably 4:1 to 1:4.

The compounds of the present invention can be preferred by glycidylating an aminophenol of the formula III

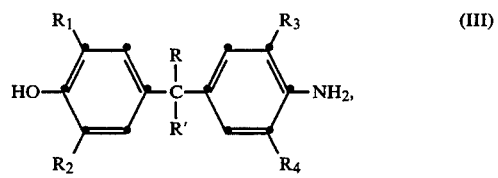

wherein R, R', $R_1$, $R_2$, $R_3$ and $R_4$ are as defined for formula I, with an epihalohydrin or glycerol dihalohydrin to give a compound of formula I.

The glycidylation of organic compounds containing hydroxyl and amino groups is a known conversion reaction. The aminophenols of formula III can be reacted, for example, with epichlorohydrin or glycerol 1,3-dichlorohydrin to give a tris(chlorohydrin) of the formula IV

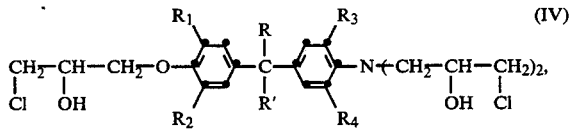

which is then dehydrochlorinated, preferably by one of the following methods:

(A) In a two step process, the aminophenol is first treated with at least 1,5, preferably with 1.6 to 5, equivalents of epichlorohydrin or glycerol 1,3-dichlorohydrin, in the presence of a Lewis acid as catalyst, to give a tris(chlorohydrin). In the second step, the tris(chlorohydrin) is treated with alkali to form the epoxy groups. The alkali is normally sodium hydroxide; but other alkalies such as barium hydroxide or potassium carbonate can also be used for converting the 1,2-chlorohydrin groups into the 1,2-epoxy groups.

(B) In the single step process, the aminophenol is treated with at least 2.5, preferably 3 to 8, equivalents of epichlorohydrin, in the presence of an alkali such as sodium hydroxide and of a phase transfer catalyst such as tetramethylammonium chloride, a tertiary amine or a quaternary ammonium base. At least a part of the excess epichlorohydrin acts as hydrogen chloride acceptor and promotes the formation of glycidyl groups, with this part of the epichlorohydrin being converted into glycerol 1,3-dichlorohydrin.

The reaction can be carried out by both methods in a solvent, for example a hydrocarbon, an ether or a ketone, although it is preferred to use an excess of epichlorohydrin as solvent in the single step process. The reaction is in general carried out at elevated temperature in the range from about 40° to 100° C. It is preferred to use those compounds of formula III wherein each of R and R' is a hydrogen atom or methyl, preferably methyl, and each of $R_1$, $R_2$, $R_3$ and $R_4$ independently is a hydrogen, chlorine or bromine atom or alkyl of up to 4 carbom atoms.

The aminophenols of formula III are known compounds. They can be obtained for example by the process described in DE patent 1 176 666 or in DE-AS 1 268 151 by reacting a bisphenol of the formula V

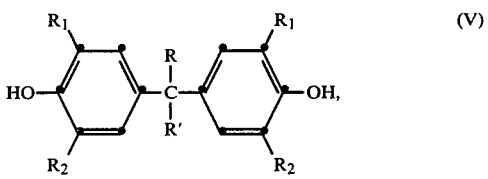

wherein R, R', $R_1$ and $R_2$ are as defined for formula I, with an unsubstituted or substituted aniline of the formula VI

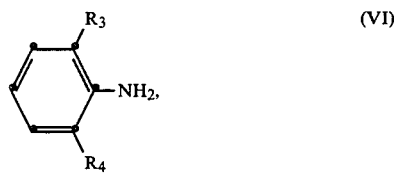

wherein $R_3$ and $R_4$ are as defined for formula I, optionally in the presence of an alkaline, but preferably of an acid, catalyst.

Examples of suitable compounds of the formula V are: bis(4-hydroxyphenyl)methane (bisphenol F), 2,2-bis(4-hydroxyphenyl)propane (bisphenol A), 2,2-bis(4-hydroxy-3,5-dibromophenyl)propane (tetrabromobisphenol A), 2,2-bis(3-methyl-4-hydroxyphenyl)propane, 2,2-bis(3-chloromethyl-4-hydroxyphenyl)propane, bis(3-tert-butyl4-hydroxyphenyl)methane and 2,2-bis(3-bromo-4-hydroxyphenyl)propane. Representative examples of substituted anilines are: 2,6-diethylaniline, 2-isopropyl-6-methylaniline, 2,6-dichloroaniline, o-chloroaniline, o-bromoaniline and o-toluidine.

The tetraglycidyl compounds of formula II contained in the epoxy resin mixtures of this invention are known e.g. from U.S. Pat. Nos. 2,921,037 and 2,951,822 and are obtained, as described therein, by glycidylating a diamine of the formula VII

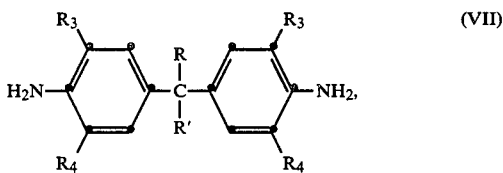

wherein R, R', $R_3$ and $R_4$ are as defined for formula II, with epihalohydrin.

The epoxy resin mixtures of this invention are preferably prepared by simply mixing a triglycidyl compound of the formula I with a tetraglycidyl compound of the formula II in the indicated ratio of epoxide equivalents. Another possibility of preparing the epoxy resin mixtures of the invention comprises glycidylating a mixture of an aminophenol of formula III and a diamine of formula VII in the appropriate equivalent ratio.

The triglycidyl compounds of this invention and mixtures thereof with tetraglycidyl compounds of formula II can be cured with the conventional hardeners for epoxy resins. Accordingly, the invention further relates to curable mixtures containing a triglycidyl compound of formula I or a mixture of a triglycidyl compound of formula I and a tetraglycidyl compound of formula II and a hardener for epoxy resins.

Typical examples of hardeners are the conventional hardeners for epoxy resins, including aliphatic, cycloaliphatic, aromatic and heterocyclic amines such as bis(4-aminophenyl)methane, aniline/formaldehyde resin, bis(4-aminophenyl)sulfone, propane-1,3-diamine, hexamethylenediamine, diethylenetriamine, triethylenetetramine, 2,2,4-trimethylhexane-1,6-diamine, m-xylylenediamine, bis(4-aminocyclohexyl)methane, 2,2-bis(4-aminocyclohexyl)propane and 3-aminomethyl-3,5,5-trimethylcyclohexylamine (isophoroediamine); polyaminoamides such as those obtained from aliphatic polyamines and dimerised or trimerised fatty acids; polyphenols such as resorcinol, hydroquinone, 2,2-bis(4-hydroxyphenyl)propane and phenol/aldehyde resins; polythiols such as the polythiols commercially available as "thiokols"; polycarboxylic acids and anhydrides thereof, for example phthalic anhydride, tetrahydrophthalic anhydride, hexahydrophthalic anhydride, hexachloroendomethylenetetrahydropthalic anhydride, pyromellitic anhydride, 3,3',4,4'-benzophenonetetracarboxylic dianhydride, the acids of the aforementioned anhydrides as well as isophthalic acid and terephthalic acid. It is also possible to use catalytic hardeners, for example tertiary amines such as 2,4,6-tris(dimethylaminoethyl)phenol, imidazoles, and other Mannich bases; alkali metal alkoxides of alcohols, e.g. the sodium alcoholate of 2,4-dihydroxy-3-hydroxymethylpentane, tin salts of alkanoic acids, e.g. tin octanoate, Friedels-Craft catalysts such as boron trifluoride and boron trichloride and their complexes and chelates which are obtained by reacting boron trifluoride with e.g. 1,3-diketones.

The suitable curing catalysts can also be used with the hardeners. Tertiary amines or salts thereof, quaternary ammmonium compounds or alkali metal alkoxides can be used as catalysts when employing poly(aminoamides), polythiols or polycarboxylic anhydrides. The amount of hardener employed depends on the chemical nature of the hardener and on the desired properties of the curable mixture and of the cured product. The maximum amount can be easily determined. If the hardener is an amine, 0.75 to 1.25 equivalents of active hydrogen bound to amino nitrogen perepoxide equivalent are normally used. If the hardener is a polycarboxylic acid or an anhydride thereof, then normally 0.4 to 1.1 equivalents of carboxyl group of anhydride group are used per equivalent of epoxy group. If the hardener is a polyphenol, it is convenient to use 0.75 to 1.25 phenolic hydroxyl groups per epoxide equivalent.

Catalytic hardeners are generally used in amounts of 1 to 40 parts by weight per 100 parts by weight of epoxy resin.

Depending on the nature of the hardener employed, curing can be effected at room temperature or at elevated temperature. If desired, curing can also be carried out in two steps, for example by discontinuing the curing procedure or, if a hardener for higher temperatures is employed, by partially curing the curable mixture at lower temperatures. The products so obtained are still fusible and soluble precondensates (B-stage resins) and are suitable for use as e.g. moulding materials, sintering powders or prepregs.

The curable mixtures of this invention can additionally contain plastifiers such as dibutyl phthalate, dioctyl phthalate or tricresyl phosphate, or additives such as extenders, fillers, reinforcing agents, colorants, plasticisers and mould release agents. Examples of suitable extenders, fillers and reinforcing agents are asbestos, asphalt, bitumen, glass fibres, textile fibres, carbon or boron fibres, mica, diatomaceous earth, gypsum, titanium dioxide, chalk, quartz powder, cellulose, kaolin, ground dolomite, wollastonite, silica gel having a large specific surface area (obtainable under the registered trademark Aerosil®), diatomaceous earth modified with long chain aines (obtainable under the registered trademark Bentone®), powdered polyvinyl chloride, polyolefines or aminoplasts, metallic powders such as aluminium or iron powder. Flame-proofing agents such as antimony trioxide can also be added to the curable mixtures.

The curable mixtures of this invention can be used for example as laminating agents, impregnating and casting resins, powder coatings, moulding materials, putties and sealing compounds, embedding compounds and insulating compounds for electrical engineering and, in particular, as adhesives or matrix resins for the manufacture of fibre-reinforced plastics materials.

EXAMPLE 1

Preparation of

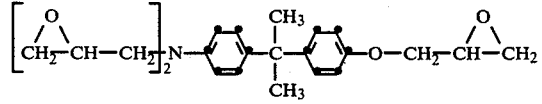

A reaction vessel equipped with stirrer, thermometer, Dean-Stark azeotropic distillation trap and dropping funnel is charged with 272.4 g (1.2 moles) of 2,2-(4-aminophenyl-4'-hydroxyphenyl)propane (prepared according to Example 2 of DE-AS 1 268 152) and 1170 g (12.62 moles) of epichlorohydrin, and the slurry is heated to 95° C. with stirring. A clear solution is obtained. Stirring is continued for 1 hour at 95° C. and then 5.81 g of a 50% aqueous solution of trimethylammonium chloride are added. The reaction solution is stirred for 2 hours at 90° to 95° C., then cooled to 20° C. and 187.2 g of a 50% aqueous solution of sodium hydroxide are added through the dropping funnel, while maintaining the temperature at 20° C. The mixture is then heated to 50° C. and, under increasing vacuum (160→53 mbar), water and epichlorohydrin are removed from the reaction solution under azeotropic conditions over 2 hours. Then 144.0 g of the 50% aqueous sodium hydroxide solution are added and the water and epichlorohydrin are removed from the reaction solution under azeotropic conditions over 2 hours at 50° C./160 mbar. After cooling to room temperature, the organic phase is extracted with methylene chloride, washed repeatedly with water, and dried over anhydrous sodium sulfate. After distillation of the residual solvent and unreacted epichlorohydrin at 50° C./20 mbar, 382 g (81% of theory) of a dark brown resin resin are obtained. Epoxide content=6.19 equivalents/kg; viscosity=5500 mPa.s$^{-1}$ at 50° C.

USE EXAMPLES

The curable mixtures given in the table, obtained from 2,2-(N,N-diglycidyl-4-aminophenyl-4'-glycidyloxyphenyl)propane (A) according to Example 1, N,N,N',N'-tetraglycidyl-4,4'-diaminodiphenylmethane (B) and 4,4'-diaminodiphenylmethane (C) as hardener, are processed to castings. This is done by preparing clear melts from the curable mixtures at 120° C., degassing them under vacuum at 20 mbar and subsequently curing them for 2 hours at 120° C., for 2 hours at 150° C. and for 2 hours at 180° C. Norm test specimens are cut from the castings and tested for the mechanical properties reported in the table.

TABLE

| Curable mixture from: | | | | | |
|---|---|---|---|---|---|
| A | 847.0 g (5 eq.) | 508.0 g (3 eq.) | 423.7 g (2 eq.) | 339.0 g (2 eq.) | 169.0 g (1 eq.) |
| B | — | 250.0 g (2 eq.) | 312.5 g (2.5 eq.) | 375.0 g (3 eq.) | 500.0 g (4 eq.) |
| C | 247.5 g (5 eq.) | 247.5 g (5 eq.) | 247.5 g (5 eq.) | 247.5 g (5 eq.) | 247.5 g (5 eq.) |
| Gel time (seconds) at: | | | | | |
| 120° C. | 750 | 890 | 830 | 1035 | 900 |
| 150° C. | 275 | 325 | 320 | 330 | 315 |
| 180° C. | 105 | 115 | 120 | 110 | 105 |
| Viscosity at 50° C. (mPas$^{-1}$) | | | | | |
| 0 min. | 4641 | 4641 | 5355 | 4284 | 6247 |
| 60 min. | 10710 | 8211 | 9639 | 6961 | 9961 |
| Deflection temperature under load according to ISO* 75 (°C.) | 159 | 186 | — | 194 | 210 |
| Flexural strength according to ISO 178 (N/mm$^2$) | 137.7 | 133.1 | — | 146.3 | 136.1 |

| TABLE-continued | | | | | |
|---|---|---|---|---|---|
| Modulus of elasticity according to ISO 178 (N/mm²) | 3772 | 3865 | — | 3840 | 3576 |

*ISO = International Standard Organization

What is claimed is:

1. A triglycidyl compound of the formula I

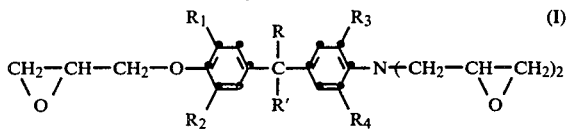

wherein each of R and R' independently is a hydrogen atom, $C_1$–$C_6$alkyl, phenyl, cyclohexyl or cyclopentyl, and each of $R_1$, $R_2$, $R_3$ and $R_4$ independently is a hydrogen atom, a halogen atom or $C_1$–$C_6$alkyl.

2. A triglycidyl compound according to claim 1, wherein each of R and R' is a hydrogen atom or methyl, and each of $R_1$, $R_2$, $R_3$ and $R_4$ independently is a hydrogen, chlorine or bromine atom or alkyl of up to 4 carbon atoms.

3. 2,2,-(N,N-Diglycidyl-4-aminophenyl-4'-glycidyloxyphenyl)propane as triglycidyl compound of formula I according to claim 1.

4. A curable mixture comprising a triglycidyl compound of formula I according to claim 1 and an effective curing amount of a hardener for epoxy resin.

5. An epoxy resin mixture containing (a) a triglycidyl compound of the formula I according to claim 1 and (b) a tetraglycidyl compound of the formula II

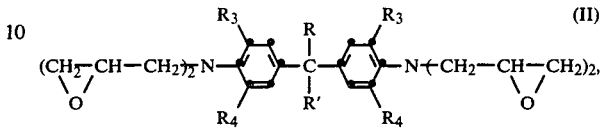

wherein R, R', $R_3$ and $R_4$ are as defined for formula I, the ratio of the epoxy equivalents of (a) to (b) in said mixture of epoxy resins being 10:1 to 1:10.

6. An epoxy resin mixture according to claim 5, containing a triglycidyl compound of the formula I and a tetraglycidyl compound of the formula II, wherein each of R and R' is a hydrogen atom or methyl, and each of $R_1$, $R_2$, $R_3$ and $R_4$ independently is a hydrogen, chlorine or bromine atom or alkyl of up to 4 carbom atoms.

7. An epoxy resin mixture according to claim 5, containing 2,2-(N,N-diglycidyl-4-aminophenyl-4'-glycidyloxyphenyl)propane as compound of the formula I and N,N,N',N'-tetraglycidyl-4,4'-diaminodiphenylmethane as compound of the formula II.

8. An exposy resin mixture according to claim 5, wherein the ratio of epoxide equivalents of (a) to (b) is 5:1 to 1:5.

9. A curable mixture comprising a mixture according to claim 5 of a triglycidyl compound of the formula I and a tetraglycidyl compound of the formula II, and an effective curing amount of a hardener for epoxy resins.

10. The mixture according to claim 5, wherein each of R and R' is a hydrogen atom or methyl, and each of $R_1$, $R_2$, $R_3$ and $R_4$ independently is a hydrogen, chlorine or bromine atom or alkyl of up to 4 carbon atoms.

* * * * *